United States Patent [19]

Dorval et al.

[11] Patent Number: 5,561,045
[45] Date of Patent: Oct. 1, 1996

[54] DETECTION REAGENT, ARTICLE, AND IMMUNOASSAY METHOD

[75] Inventors: Brent L. Dorval, Douglas; Lilibeth K. Denham; Walter Keil, both of Cambridge; Alexander M. Klibanov, Newton, all of Mass.

[73] Assignee: Intracel Corporation, Cambridge, Mass.

[21] Appl. No.: 177,732

[22] Filed: Jan. 4, 1994

[51] Int. Cl.⁶ .................... G01N 33/543; G01N 33/569
[52] U.S. Cl. .................... 435/5; 435/7.92; 435/7.94; 435/7.95; 435/971; 435/973; 435/805; 436/513; 436/518; 436/523; 436/533; 436/828; 422/56
[58] Field of Search ................ 435/5, 973, 971, 435/7.9, 7.92, 7.94, 7.95, 805; 436/513, 828, 518, 523, 525, 527, 533; 422/56

[56] References Cited

U.S. PATENT DOCUMENTS

| | | | |
|---|---|---|---|
| 3,951,748 | 4/1976 | Devlin | 435/7.3 |
| 4,066,403 | 1/1978 | Bruschi . | |
| 4,098,645 | 7/1978 | Hartdegen et al. | 435/182 |
| 4,248,829 | 2/1981 | Kitajima et al. . | |
| 4,366,241 | 12/1982 | Tom et al. | 435/7.91 |
| 4,373,932 | 2/1983 | Gribnau et al. | 436/805 |
| 4,407,943 | 10/1983 | Cole et al. . | |
| 4,469,787 | 9/1984 | Woods et al. | 435/7.4 |
| 4,472,508 | 9/1984 | Ingbar | 436/500 |
| 4,474,878 | 10/1984 | Imagawa et al. | 435/810 |
| 4,511,662 | 4/1985 | Baran et al. | 436/513 |
| 4,604,208 | 8/1986 | Chu et al. | 210/650 |
| 4,654,299 | 3/1987 | Lentfer | 436/531 |
| 4,703,018 | 10/1987 | Craig et al. | 436/518 |
| 4,704,366 | 11/1987 | Juarez-Salinas et al. | 436/501 |
| 4,757,002 | 7/1988 | Joo | 435/7.92 |
| 4,757,014 | 7/1988 | Hendrickson et al. | 436/531 |
| 4,780,422 | 10/1988 | Mitani et al. | 436/524 |
| 4,803,171 | 2/1989 | Baier et al. | 436/530 |
| 4,808,529 | 2/1989 | Doppelfeld et al. | 435/179 |

(List continued on next page.)

FOREIGN PATENT DOCUMENTS

| | | |
|---|---|---|
| 0152305 | 8/1985 | European Pat. Off. . |
| 0299359 | 1/1989 | European Pat. Off. . |
| 0308232 | 3/1989 | European Pat. Off. . |
| 430517A2 | 6/1991 | European Pat. Off. . |
| 513560A1 | 11/1992 | European Pat. Off. . |
| 0537827 | 4/1993 | European Pat. Off. . |

OTHER PUBLICATIONS

Johnstone, A., & Thorpe, R. Immunochemistry in Practice, Boston: Blackwell Scientific Publications, 1987, pp. 214–225.

Tijssen P. Practice & Theory of Enzyme Immunoassays Laboratory Techniques in Biochemistry and Molecular Biology, vol. 15, New York: Elsevier, 1985, pp. 329–349.

Chemical Abstracts, 1–Pharmacology, vol. 106, No. 15, Apr. 13, 1987, pp. 1 and 458.

Gribnau, T., et al., "DIA—Disperse Dye Immunoassay", Affinity Chromatography and Biological Recognition, 1983, Academic Press pp. 375–380.

Gribnau, T., et al., "The Application of Colloidal Dye Particles as Label in Immunoassays: Disperse(d) Dye Immunoassay (DIA)", Affinity Chromatography and Related Techniques, 1982, Elsevier Scientific Publishing pp. 411–424.

Micro Filtration Systems Catalog (1981), pp. 14–15.
Millipore Direct Catalog (1991–1992), pp. 16–18.

Primary Examiner—James C. Housel
Assistant Examiner—Christopher L. Chin
Attorney, Agent, or Firm—Wolf, Greenfield & Sacks, P.C.

[57] ABSTRACT

The binding site on an immunoglobulin for a protein is blocked by hydrophobically coupling the immunoglobulin to a blocking agent such as a label. This results in a detection reagent useful in a variety of test assays in which a protein and an immunoglobulin are advantageously used together, but separately. The reagent is useful in the simultaneous determination of IgG and one of IgA or IgM. Anti-IgA-IgG or anti-IgM-IgG is coupled to a hydrophobic label, particularly a pigment or dye, which label blocks the binding site on IgG for Protein A, and labeled Protein A is added.

21 Claims, 2 Drawing Sheets

U.S. PATENT DOCUMENTS

| | | | |
|---|---|---|---|
| 4,829,012 | 5/1989 | Cambiaso et al. | 436/512 |
| 4,874,813 | 10/1989 | O'Shannessy | 525/54.1 |
| 4,912,034 | 3/1990 | Kalra et al. | 422/56 |
| 4,921,878 | 5/1990 | Rothman et al. | 521/53 |
| 4,952,519 | 8/1990 | Lau | 525/54.1 |
| 4,956,303 | 9/1990 | Self | 436/542 |
| 4,959,307 | 9/1990 | Olson | 422/56 |
| 4,962,023 | 10/1990 | Todd et al. | 435/7.92 |
| 5,008,078 | 4/1991 | Yaginuma et al. | |
| 5,028,657 | 7/1991 | Hsu et al. | 525/54.1 |
| 5,075,215 | 12/1991 | Dreyer | 435/6 |
| 5,093,230 | 3/1992 | Osther et al. | 435/5 |
| 5,132,206 | 7/1992 | Dreyer | 435/6 |
| 5,191,066 | 3/1993 | Bieniarz et al. | 530/391.1 |
| 5,206,136 | 4/1993 | Monji et al. | 435/5 |
| 5,219,763 | 6/1993 | Van Hoegaerden | 436/523 |
| 5,252,459 | 10/1993 | Tarcha et al. | 422/61 |
| 5,286,452 | 2/1994 | Hansen | 422/73 |
| 5,308,580 | 5/1994 | Clark | |

Fig. 1a  DISEASE

Fig. 1d  NO DISEASE

DETECTION REAGENT, ARTICLE, AND IMMUNOASSAY METHOD

This application is being filed concurrently with a commonly-owned U.S. Patent Application entitled "Radial Flow Assay", by Dorval et al., which is incorporated herein by reference for all purposes.

FIELD OF THE INVENTION

The present invention relates generally to assay reagents, methods, and apparatus, and more particularly to an immunoassay exploiting the specific interaction of both an antibody and a protein as determining species in a single determination.

BACKGROUND OF THE INVENTION

Immunoassays have been used for many years in the detection of agents in samples. Such assays can be used to detect the presence of unwanted agents in a sample of fluid, for example the presence of bacteria in a bodily fluid or a pollutant in water. They can be used also to test for the presence of antibodies in body fluids, as an indication of the presence of an infectious agent, a cancer cell or an autoimmune disease.

Although many such assays represent extraordinary improvements over the prior methodology for determining the presence of an agent in a sample, the goal remains to develop immunoassays that are rapid and sensitive. It is a drawback of almost every immunoassay presently in use that the assay either is too slow (5–30 minutes) or, if faster, is not sufficiently sensitive (or both). Where the detection of disease is concerned, it is unacceptable to compromise on sensitivity, and accordingly those assays that are among the most sensitive tend to be cumbersome and slow.

Antibodies of the classes including IgA, IgG, or IgM specific for a particular antigen may be produced by animals at various disease stages. One or more classes prevail at different times. Ideally, the presence of all classes of antibodies specific for a particular antigen would be determined in a single assay. Such an assay would be highly sensitive because it would ensure detection of the presence of the prevalent class of antibody. However, heretofore known immunoassays do not achieve such sensitivity, due in large part to problems that result from unwanted specific binding and/or aggregation between species in test assay reagents, or unwanted binding between a test assay reagent and an analyte. To determine antibodies of a single class in a sample, assays have been developed that involve time-consuming analysis in which unwanted classes of antibodies are selectively removed from the sample solution prior to analysis of the antibody class of interest. Such a method is described in U.S. Pat. No. 4,829,012, issued May 9, 1989 to Cambiaso et al., in which the antibody class of interest is measured, after such selective removal, by inducing agglutination, and measuring the degree of agglutination. However, as a result of these problems, most assays measure the presence of only a single class of immunoglobulin, e.g. IgG.

One complication hindering development of an assay determinative of any or all of IgA, IgG, or IgM specific for a particular antigen in a single procedure is the fact that conventional proteins and antibodies that serve as binding partners for capturing antibodies of various classes also tend to bind to each other. Specifically, Protein A binds IgG, and this binding may be exploited in the determination of the presence of IgG. If the presence of IgA or IgM is to be determined, then anti-IgA or anti-IgM of the IgG class typically is utilized. The simultaneous determination of IgG using Protein A, and IgA or IgM using anti-IgA and/or anti-IgM of the IgG class according to heretofore known techniques, however, is complicated, as the assay reagents Protein A and anti-IgA or anti-IgM bind to each other. For that matter, the determination of any species in a sample using Protein A and a binding partner of the IgG class is complicated when performed according to known techniques.

Immunoassays also typically involve some kind of label for detecting the presence of the binding between an antibody and an analyte. Radioisotopes have commonly been used, but such use is discouraged for reasons including safety. Fluorophores, enzymes, chemiluminescent species, and the like also have been employed as labels in immunoassays. U.S. Pat. No. 4,373,932, issued Feb. 15, 1983 to Gribnau et al., describes reagents and test kits for the determination of immunochemically reactive components, in which one or more labeled species are attached to particles of an aqueous dispersion of a hydrophobic dye or pigment, or of polymer nuclei coated with such a dye or pigment. The use of such dyes offers many advantages, including safety and cost. The use of dyes in immunoassays, however, has not achieved widespread use perhaps because of problems with detection.

SUMMARY OF THE INVENTION

The present invention is directed to products and processes that permit, among other things, the ability to detect simultaneously a variety of classes of immunoglobulin specific for the same analyte. The invention thereby enhances the sensitivity of immunoassays by employing the reagents of the invention and also permits such immunoassays to be performed more rapidly. The invention also expands the possible uses of specific binding proteins such as Protein A and Protein G, and also expands the possible uses of dyes, pigments and the like in immunoassays.

According to one aspect of the invention, a detection reagent for use in a test assay is provided. The detection reagent includes an immunoglobulin, belonging to a class, that specifically binds to a predetermined analyte. The reagent also includes a detection agent such as a protein that binds to a binding site on an Fc region of immunoglobulins of that class. A blocking agent is hydrophobically coupled to the immunoglobulin in a manner to block the binding site on the immunoglobulin from interaction with the protein. The protein and immunoglobulin thus can be used simultaneously in an immunoassay to detect, for example, a plurality of classes of immunoglobulin simultaneously. Either or both of the immunoglobulin and the protein may be labeled.

The particular blocking agent described in the preceding paragraph is hydrophobically coupled to the immunoglobulin to block the binding site from interaction with the protein. Blocking means physically interfering with the binding interaction between the binding site and the blocking agent by, for example, covering or masking part of or all of the binding site, interfering with access of the protein to the binding site (sterically or by charge), or otherwise interfering with binding. Blocking agents generally include any molecular species that can be bound to an immunoglobulin by covalent or noncovalent forces. Preferred blocking agents are those that include hydrophobic regions, permitting hydrophobic binding between the Fc portion of the immunoglobulin and the blocking agent. Most preferred are those that can perform a dual function, that is, blocking of a binding site on the Fc region of an immunoglobulin and labeling of that immunoglobulin so as to permit detection of the presence of that immunoglobulin in the binding assays of the invention. The immunoglobulin may be associated with blocking agents such as particulate dispersions that are labels. In this manner, noncovalent, hydrophobic bonds of high strength are formed simply by mixing the immunoglobulin with the blocking agent. The immunoglobulin is then both labeled and blocked from interaction with the protein.

The preferred binding site is a hydrophobic region of the Fc portion of the immunoglobulin, and a particularly preferred binding site is a hydrophobic region of the constant heavy II portion of the immunoglobulin. Blocking agents thus may be bound to the immunoglobulin in a manner such that they do not interfere with the binding specificity of the immunoglobulin.

The preferred immunoglobulins are anti-IgA-IgG and anti-IgM-IgG. The preferred protein is Protein A.

According to another aspect of the invention, a device useful in an immunoassay is provided. The device includes a support having hydrophobic regions. An immunoglobulin is coupled to that support by hydrophobic coupling between an Fc binding site of the immunoglobulin and one of the hydrophobic regions of the support. The support also has bound to it a protein that is capable of binding to a binding site on an Fc region of the immunoglobulin, but the protein and the immunoglobulin are free of hydrophobic coupling between them on the support of the invention. The foregoing can be accomplished, for example, according to methods of the invention which involve blocking the binding site for the protein on the immunoglobulin by employing the support essentially as a blocking agent, as discussed above. The interaction between the immunoglobulin and the support interferes with the ability of the protein to bind to the immunoglobulin. Thus, immunoglobulin first may be applied to the support, followed by application to the support of the protein. Wash steps may follow either or both of the steps of applying immunoglobulin and applying protein to the support. Both immunoglobulin and protein then will be bound to the support by hydrophobic coupling, but will be free of interaction between them, such as hydrophobic coupling. Both likewise will be free to interact specifically with analytes in a sample. The preferred supports are plates, beads, laboratory apparatus surfaces, water insoluble particulate species, and porous membranes, and include labels such as dye particles and pigment particles.

According to another aspect of the invention, a method of capturing a binding partner of an immunoglobulin belonging to a class, in the presence of a protein is provided. The method involves contacting a sample suspected of containing the binding partner simultaneously with an immunoglobulin and a protein that binds to a binding site on the Fc region of that immunoglobulin. The binding site on the immunoglobulin, however, is blocked thereby preventing interaction between the protein and the immunoglobulin. The immunoglobulin and protein may be free in solution or one or both may be coupled to a support, preferably hydrophobically. If coupled to a support, the preferred support is selected from the group consisting of dye particles and pigment particles.

According to another aspect of the invention, a method of preparing a test assay reagent is provided. The method involves blocking a binding site for a protein on an immunoglobulin that specifically binds to a predetermined analyte, and then providing the immunoglobulin together with the protein. The immunoglobulin may be provided, for example, together with the protein in solution in a single test assay reagent. These reagents also may be provided together, but packaged separately in a kit. Preferably, the binding site is blocked by hydrophobically coupling a blocking agent to the immunoglobulin, and most preferably the binding site is blocked by hydrophobically coupling a label such as a dye or a pigment to the immunoglobulin. The protein can be labeled with a dye or pigment as well. Most preferably the protein is Protein A.

According to another aspect of the invention, a method for determining at least one analyte in a sample is provided. The method involves contacting a sample suspected of containing the at least one analyte with a detection reagent. The detection reagent includes a protein and an immunoglobulin that specifically binds to the analyte. The binding site for the protein on the immunoglobulin is blocked, and a label is coupled to the immunoglobulin. The label then is detected. Preferably the method involves the detection of at least two immunoglobulins. Thus, the preferred analytes are immunoglobulins. The sample is preferably contacted with a detection reagent comprising Protein A and IgG that specifically binds to the at least one analyte. Preferably the IgG carries a label, and a binding site on the IgG for the Protein A is blocked. The binding site may be blocked with a species hydrophobically coupled to the IgG.

According to another aspect of the invention, an improvement to immunoassays of the type employing a plurality of binding partners to determine the presence of a plurality of analytes is provided. The improvement involves the simultaneous use, as binding partners to determine a plurality of analytes in a solution, of a protein that binds to a binding site on an Fc region of an immunoglobulin of a class, and an immunoglobulin of that class that specifically binds to a predetermined analyte. Preferably the protein is Protein A and the immunoglobulin is of the IgG class. Most preferably the immunoglobulin binds specifically to an immunoglobulin of a different class such as IgA or IgM.

The invention also provides a wide variety of kits including the detection reagents described above or precursors to those detection reagents. The preferred kit includes a package that contains both a protein that binds to a binding site on an Fc region of an immunoglobulin of a class. The immunoglobulin specifically binds to a predetermined analyte, and a binding site for the protein on that immunoglobulin is blocked.

A particularly useful detection reagent formulation includes Protein A and immunoglobulin G (IgG). The IgG may be a species such as anti-IgA of the IgG class (anti-IgA-IgG) or anti-IgM of the IgG class (anti-IgM-IgG), or both. The species (or these species) may be labeled and used together with labeled Protein A as a single assay detection reagent. A sample suspected of containing IgM and/or IgA, along with IgG, may be contacted with this detection reagent, and the presence of IgM and/or IgA, as well as IgG, determined without unwanted binding between any species in the detection reagent and any analyte, or between any two species in the detection reagent. Any or all labels then may be detected.

BRIEF DESCRIPTION OF THE DRAWINGS

FIGS. 1a–1f schematically illustrate a test assay procedure for the determination of both IgG and one of IgA, IgM, or a combination in a single sample according to one of embodiment of the invention; and FIGS. 2a–c illustrate the appearance of a test assay surface according to one embodiment of the present invention after a test assay as illustrated in FIG. 1 has been performed in which the result is error, negative, and positive, respectively.

DETAILED DESCRIPTION OF THE PREFERRED EMBODIMENTS

Many pairs of biological species exhibit mutual affinity, or mutual binding capacity, typically defined by specific or non-specific binding or interaction. Such interaction generally occurs between pairs of molecular species in which one member possesses one or more particular exposed areas which bind to one or more particular exposed areas of the other member of the pair. The exposed areas allowing such binding are typically defined by specific spatial and/or polar organization. The term "binding partners" may be used, and is used herein, to define pairs of species exhibiting such mutual affinity. For example, such binding partners include antibody/antigen, antibody/hapten, enzyme/substrate, enzyme/inhibitor, enzyme/cofactor, biotin/avidin, binding protein/substrate, carrier protein/substrate, lectin/carbohydrate, receptor/hormone, receptor/effector, complementary strands of nucleic acid, repressor/inducer, and the like. The physical association of binding partners may be by interaction of hydrophilic groups, which is typical of most reversible biological interactions. Such physical association may also be by interaction of hydrophobic groups, which association can rival or exceed the strength of covalent bonds.

Binding of antibodies to molecular species typically involves the highly specific interaction of the variable portion of the antibody with the molecular species. This interaction, or specific binding as used herein, is responsible for the specific recognition by antibodies of foreign substances. Binding, however, also may occur between a molecular species and the constant region of the antibody. Such binding may be specific as by Protein A recognition or may be non-specific such as by hydrophobic interaction with any of a wide variety of hydrophobic species.

Interaction of Protein A and an antibody generally occurs via interaction of the protein with the constant heavy II region of the antibody. This binding may be useful when it is desirable to determine the presence or amount of a particular class of antibody in a sample, i.e. the presence of IgG. However, such binding adds complication to any test assay procedure in which it would be desirable to use simultaneously both Protein A and antibodies of the IgG class for identifying a plurality of analytes.

For example, it would be advantageous to detect, simultaneously, immunoglobulins including those of the classes IgG, IgA, and IgM in a single test assay so that if any of these antibodies had been produced by an animal in response to a particular infections agent, such production could be detected, and the presence of infection implied. Labeled Protein A may be used to determine the presence of IgG, and labeled anti-IgA-IgG may be used to determine the presence of IgA. Similarly, anti-IgM-IgG may be used to determine IgM. If, however, such agents were used together, then the labeled Protein A would bind to the labeled anti-IgA-IgG and anti-IgM-IgG, causing aggregation and hindering the assay.

It has been determined in accordance with the present invention that a blocking agent may be hydrophobically coupled to an immunoglobulin to block a binding site on an Fc region thereof, thereby preventing a protein that binds to that site from attaching to the Fc region of the immunoglobulin. Blocking of immunoglobulin/protein interaction in accordance with the present invention may be effected by allowing a hydrophobic patch on an immunoglobulin to interact closely with a hydrophobic region of a blocking agent or support by contacting the two with each other in an aqueous environment. In such an environment, solvent molecules (water) associate with each other rather than associating with the hydrophobic patch of the immunoglobulin or hydrophobic region of the blocking agent or support, allowing the two to come into very close proximity. Then, forces such as van der Waals forces, London forces, electrostatic forces, hydrogen bonding, and the like cause strong, yet noncovalent coupling between the hydrophobic patch and hydrophobic region. As used herein, the term "hydrophobic coupling" will refer to this interaction. Such coupling can result in an equilibrium constant of coupling of from about $\mathbf{10}^{14}$ to the $\mathbf{10}^{15}$.

A wide variety of blocking agents and supports having hydrophobic regions may be caused to couple to immunoglobulins according to the present invention. Included are water insoluble particulate species, such species made up of small particles or aggregations of small particles insoluble in an aqueous medium, or any material forming a suspension or dispersion of such small particles or aggregations of small particles when introduced into an aqueous medium.

According to one embodiment of the invention, the blocking agent and the support are one and the same. Any blocking agent may serve as a support in accordance with the invention so long as it can carry an immunoglobulin and a protein both coupled to the blocking agent, the protein being of the type that binds to a binding site on an Fc region of the immunoglobulin, with the protein and immunoglobulin being free of any interaction such as hydrophobic coupling between them.

An exemplary list of classes of blocking agents and supports useful for hydrophobic coupling to antibodies in accordance with the present invention includes organic and inorganic surfaces and particles such as glass plates or beads, laboratory apparatus surfaces such as test tube walls, plates such as titer plates, ceramic surfaces and particles, plastic surfaces and particles, silanized surfaces and particles, polymeric beads, magnetic particles such as magnetic metal particles, gels such as sephadex gel, silica, dried silica gel, wollastonite, bentonite, alumina, hydroxy apatite, porous membranes, hydrophobic carriers containing an attached label, and labels themselves.

According to one embodiment of the invention, a label itself defines a water-insoluble particulate species that serves as a blocking agent. As used herein the term "label" means those molecular entities that are useful in detecting the presence of an antibody/analyte interaction. Such labels are well known to those of ordinary skill in the art and are discussed briefly in the background above. A wide variety of labels may be selected, including but not limited to chromophores; fluorophores; metal sols such as gold, silver, platinum, copper, iron, and the like; metal halides including silver halides; metal oxides and hydrous oxides including copper hydrous oxide, iron oxide or hydroxide; indirect labels such as enzymes, e.g. alkaline phosphatase and horse radish peroxidase used with a developing reagent; radiolabels; finely divided polymer particles such as latex or polystyrene particles, including colored polymeric particles such as those described in U.S. Pat. No. 5,252,459, issued Oct. 12, 1993 to Tarcha et al. and incorporated herein by reference; inorganic hydrophobic composite particles such as those described in U.S. Pat. No. 4,780,422, issued Oct.

25, 1988 to Mitani et al. and incorporated herein by reference; dyes; pigments; and the like.

Figure 1B:
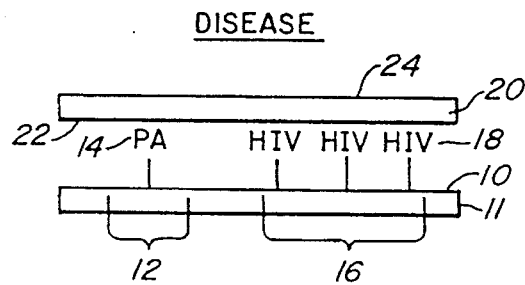
Figure 1B:
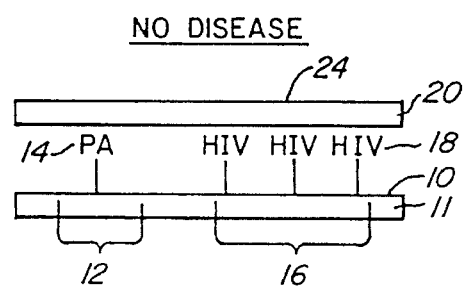
Figure 1B:
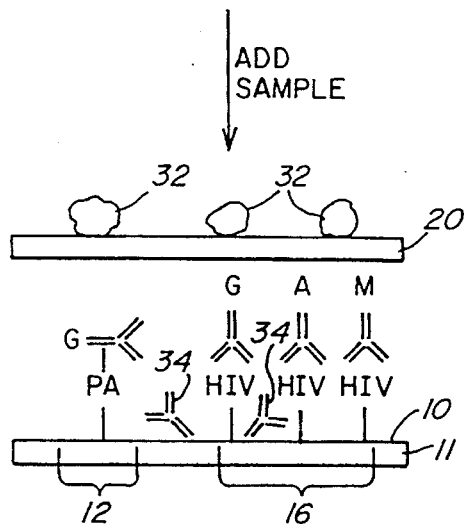
Figure 1E:
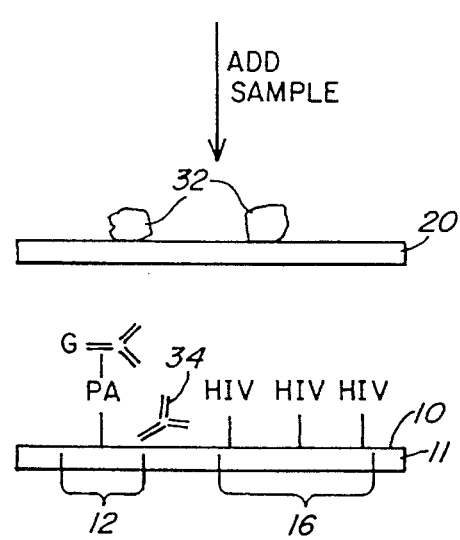
Figure 1C:
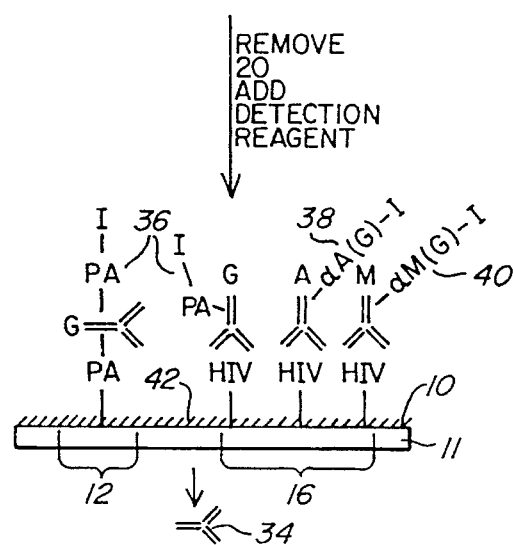
Figure 1F:
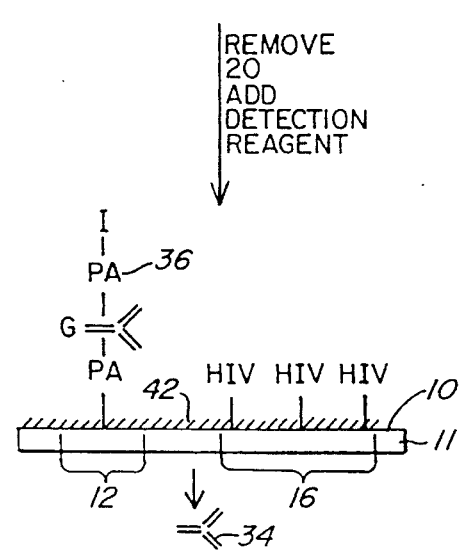

Preferred are those labels that can be readily detected visually with the naked eye or with the aid of an optical filter and/or applied stimulation, for example via colorimetry, fluorimetry, or atomic absorption spectrophotometry, and particularly preferred are dyes and pigments. Virtually any dye or pigment forming a particulate suspension or dispersion in an aqueous environment, that is, dyes having a substantial degree of hydrophobicity, may be selected as a label for blocking a binding site for a protein on an immunoglobulin in accordance with the present invention. A non-limiting, exemplary list of dyes suitable for use includes water soluble dyes that have been made water insoluble such as via cross-linking; leuco-vat dyes converted by oxidation or provided in sulphate half-ester form; other dyes made insoluble through oxidation or via diazo coupling; natural dyes; synthetic dyes; disperse dyes; solvent dyes; sulphur dyes; mordant dyes; leuco sulphur dyes; azoic dyes; azo dyes including monoazo, diazo, triazo, tetrazo etc.; oxidation bases; ingrain dyes; transfer dyes; quinoline dyes; triarylmethane dyes; acridine dyes; alizarin dyes; phthaleins; insect dyes; lake-type certified dyes; anthraquinoid dyes; cyanine dyes; phenazathionium dyes; phenazoxonium dyes; cationic dyes; metal dyes such as Alizarin Cyanin RR, Alizarin Green sulfur, Nigrosine 2Y, Naphthalene Blue RS, etc.; reactive dyes; fluorescent bleaching dyes; disperse dyes; acid dyes; xanthene dyes; and the like. Suitable dyes also are described in U.S. Pat. No. 4,780,422, referenced above, and U.S. Pat. No. 4,373,932, issued Feb. 15, 1983 to Gribnau et al. incorporated herein by reference.

Suitable pigments include, but are not limited to, inorganic pigments including oxides and sulfides of metals such as aluminum, antimony, iron, titanium, zinc, cobalt, and chromium; hydrated metal oxides; metal sulfates such as lead sulfate; metal carbonates such as lead carbonate; suspensions of metal powder such as gold and aluminum; earth colors such as siennas, ochers, and umbers; lead or strontium chromates; carbon black; crystalline silica; organic pigments including animal pigments such as rhodopsin and melanin, plant and vegetable pigments such as chlorophylls, carotenoids including carotene and xanthophyll, indigo, flavanoids including catechins, flavones, flavanols, anthocyanins, flavanones, leucoanthocyanidins, flavanols; synthetic pigments such as phthalocyanine, lithos, toluidine, para red, toners; chlorinated or non-chlorinated copper phthalocyanine pigments; triphenylmethane pigments; and triarylmethane pigments. For example, pigments such as $C_{32}H_{16}N_8Cu$, $C_{32}H_{28}N_3O_4SNa$, $C_{37}H_{34}N_2O_9S_3Na_2$, $C_{32}O_{0-1}N_8$ $Cl_{15-16}Cu$, and barium potassium chromate may be used. Additionally, Red 17 and Violet 23, available from Sun Chemical Company, Cincinnati, Ohio may be used. Particulate dispersions of such labels may be prepared as described in "The Chemistry of Synthetic Dyes", Academic Press, New York, Vol I (1952), III 9 1952), III (1970), IV (1971), V (1971), VI (1972), VII (1974), VIII (1978), Venkataraman (Ed.), and in "Colloid Science", Vol. I, Elsevier, Amsterdam, Kruyt (Ed). Such dyes and pigments offer the advantage of being detectable with the naked eye, and optionally may be dissolved in an organic solvent for final determination.

When a dispersion of water-insoluble particulate label is formed in an aqueous environment containing immunoglobulins, the immunoglobulins become hydrophobically coupled to the particulate label as described above, and are blocked with respect to biological binding with proteins that bind the Fc region of the immunoglobulin. The specific binding capability of the immunoglobulin, however, remains intact. The immunoglobulins then may be separated from aqueous solution via centrifugation, filtration, or the like and used as a reagent in a test assay. The hydrophobic coupling between antibody and hydrophobic dye or pigment takes place within about one-half hour at room temperature, and the interaction is extremely strong, as repeated (at least five times) re-suspension and centrifugation of the reagent does not diminish the sensitivity of the reagent in test assays.

As noted above, according to one embodiment of the test assay detection reagent, it is preferred that the blocking agent performs a dual function of blocking a binding site on the Fc region of an immunoglobulin and labeling of that immunoglobulin. However, the Fc region may be blocked as described above, and a separate label attached to the immunoglobulin.

Particulate label, including dye and/or pigment particles, of a variety of sizes may be used in accordance with the present invention. It is important only that the dye or pigment particles used are of a size allowing adequate detection in an assay. The preferred particulate label has a size distribution of from about 10 nm to about 15 microns, more preferably from about 100 nm to about 8 microns, and still more preferably from about 500 nm to about 5 microns. Additionally, when a test assay solid phase such as that described in the above-referenced co-pending application entitled "Radial Flow Assay", by Dorval et al. is utilized, it is advantageous to select dye or pigment particles having a dimension of from about 0.1 micron to about 5 micron, preferably from about 0.5 micron to about 2 microns.

Blocking of the binding between a protein and the Fc region of an immunoglobulin according to the invention finds use in a wide variety of applications. For example, one or more analytes may be determined by contacting a sample suspected of containing the analyte or analytes with a detection reagent including a protein, and an immunoglobulin that specifically binds to one of the analytes, and allowing the immunoglobulin to capture one of the analytes. The immunoglobulin carries an attached label, and a binding site for the protein on the immunoglobulin is blocked. The protein may also carry an attached label, and may also be allowed to capture one or more analytes. The sample may be a fluid sample having analyte dispersed or dissolved therein. The labels then may be detected by capturing either or both of the analyte/immunoglobulin or analyte/protein complex. As used herein, the term "capture" refers to the analysis, recovery, detection, or other qualitative or quantitative determination of a member of a binding partner pair in a particular medium.

For example, following the step of contacting the sample with the detection reagent, the sample/detection reagent solution or dispersion may be contacted with a test assay surface carrying an immobilized binding partner of the analyte, the protein, and/or the immunoglobulin. The label may then be detected at the test assay surface. Optionally, the sample may first be brought into contact with a test assay surface carrying an immobilized binding partner of the analyte. As used herein, the term "sample" is meant to encompass this arrangement, in which an analyte in a sample has been captured by a binding partner immobilized at a test assay surface. The sample (sample analyte immobilized at the test assay surface) may then be contacted with a detection reagent including a protein and an immunoglobulin that specifically binds to the analyte, the immunoglobulin being labeled and blocked, as described above. The label may then be detected.

According to another embodiment, an immunoglobulin belonging to a class may be hydrophobically coupled to a support having hydrophobic regions, such coupling blocking the affinity of immunoglobulin for a protein that binds to the Fc region of the immunoglobulin. Such a protein that binds to a binding site on an Fc region of immunoglobulins of the class may then be immobilized on the same support without interference that otherwise would be caused by binding of the protein to the immunoglobulin. The immunoglobulin and protein, each bound to the support, may then be used in a test assay to capture binding partners of either or both. For example, if anti-IgA-IgG is first coupled to a support, followed by coupling of Protein A to the support (with wash steps optionally following the coupling steps), the resulting support-immobilized Protein A and IgG could be utilized independently of each other to capture, respectively, IgG and IgA. Such an arrangement could find use in the detection of autoimmune disease.

The sensitivity of a wide variety of test assays may be enhanced by hydrophobically coupling an immunoglobulin to a blocking agent to block immunoglobulin/Protein A affinity in accordance with the present invention. For example, direct, indirect, competitive, and sandwich type heterogeneous or homogeneous assays such as those described in U.S. Pat. No. 5,252,459, may be performed with reagents and/or in accordance with methods of the present invention. Thus, it will be understood that the reagents of the invention may be used advantageously in virtually any type of immunoassay wherein it is desirable to prevent the interaction of a protein such as Protein A with the Fc portion of an immunoglobulin. Thus, antigen may be bound to a solid phase, and the presence of different classes of antibodies specific for that antigen in a sample may be determined. Likewise, either or both of the blocked immunoglobulin and protein may be bound to a solid support according to the invention. Those of ordinary skill in the art will also recognize that the advantages extend also to immunoassays that do not utilize a solid support, but instead are carried out in solution.

Significant sensitivity in analyte detection is obtained according to the present invention. As an example, in the detection of HIV infection, it is desirable to detect antibodies of all of the classes IgA, IgG and IgM produced in response to the HIV virus, such that presence of the disease may be positively determined over as wide a range of disease stages as possible. Heretofore known assays can not detect antibodies of all three of these classes simultaneously, thus such an assay may fail to show a positive result when antibody is present in a sample (that is, when infection is present).

According to one aspect of the present invention, HIV virus (HIV-1 and/or HIV-2), or an antigenic determinant thereof, may be immobilized on a test assay surface of an assay solid phase. As used herein, the term "immobilization" is meant to define covalent or absorptive attachment to a surface of a test assay solid phase in such a way that detachment from the solid phase does not occur during the assay protocol. The term "assay solid phase" is meant to define a solid phase support upon a surface of which an assay reagent may be immobilized, and which is insoluble in sample components, detection reagents or other species with which it comes into contact during a test assay. The immobilized HIV virus (or antigenic portion thereof) then may be contacted with a sample, whereupon immunoglobulins of the classes IgA, IgG, and/or IgM produced as antibodies in response to HIV infection, if present, will bind to the immobilized HIV virus. A detection reagent may be prepared with labeled Protein A, labeled anti-IgA-IgG, and labeled anti-IgM-IgG, where each of the labeled anti-IgA and anti-IgM are hydrophobically coupled to a blocking agent blocking interaction of the labeled immunoglobulin with Protein A. Preferably, these labeled immunoglobulins are blocked with the label itself, and the detection reagent includes labeled Protein A, labeled and blocked anti-IgA-IgG, and labeled and blocked anti-IgM-IgG. The detection reagent then may contact the assay surface, the presence of label on the surface signifying the presence of antibody to HIV in the sample, i.e. a positive result. Protein A is preferred in this assay, due to its relatively low cost. Nevertheless, Protein G can be substituted. Interspecies anti-IgG of the IgG class also can be substituted.

As another example, if it were desirable to detect IgA and IgM that specifically bind to HIV virus, and it were desirable to use anti-IgA of the IgG class and anti-IgM of the IgA class in a single reagent, then the binding of the anti-IgA-IgG and anti-IgM-IgA could be blocked, as described above, by hydrophobically coupling a blocking agent to the anti-IgM-IgA. These and other modifications and equivalents will be readily apparent to those of ordinary skill in the art.

It is to be understood that the present invention is not limited to applications which utilize proteins that bind the Fc region of an immunoglobulin (e.g. Protein A, Protein G, immunoglobulins with Fc specificity and the like). The invention is useful whenever it is desirable to prevent the interaction of two detection agents with one another. It is important only that the two detection agents have a tendency to bind in an unwanted fashion with one another, and that this binding can be blocked with a blocking agent, preferably by hydrophobic coupling, without interfering with the detection specificity of the detection agent.

As mentioned above, the reagents of the invention can be used in virtually any immunoassay format. Referring now to FIGS. 1a–1f, an exemplary immunoassay is illustrated, utilizing test assay reagents in accordance with the present invention and an assay kit including a particular device described in greater detail in the above-referenced, co-pending, commonly-owned U.S. Patent Application entitled "Radial Flow Assay", by Dorval et al. At FIG. 1a, the kit includes a porous delivering member 20 comprised of two membranes in face to face relation, one serving as a prefilter and having a delivering surface 22, and one serving as a diffusing material mounted opposite the delivering surface 22. The separate membranes defining delivering member 20 are not illustrated in FIG. 1. Delivering surface 22 of delivering member 20 may be held in even contact with test assay surface 10 of a test assay solid phase 11, as it is conformable to test assay surface 10. Delivering member 20 is constructed so as to evenly wet test assay surface 10 with a fluid sample. The kit utilizes a detection reagent in accordance with the present invention including a labeled protein, and labeled antibodies specific for a predetermined analyte, the labels blocking a binding site for the protein on the antibodies. Specifically, a highly-sensitive HIV detection assay according to the present invention is illustrated. With reference to FIG. 1, the assay also includes Protein A as a first immobilized assay reagent 14 and HIV as a second immobilized assay reagent 18 on first area 12 and second area 16, respectively, of test assay surface 10.

To perform the assay, delivering member 20 is placed upon test assay solid phase 11 such that delivering surface 22 evenly contacts test assay surface 10. Sample is added to sample receiving surface 24 of delivering member 20 (FIGS. 1b, 1e, preferably substantially in the center of surface 24, whereupon the sample is rapidly radially diffused by a diffusing material (not illustrated). Delivering member 20 filters the sample of particulate material 32 of a dimension larger than the smallest pore dimension of delivering member 20, and evenly transfers sample to test assay surface 10.

After a sample has been delivered to test assay surface 10 via delivering member 20, any binding partners of first or second immobilized assay reagents 14 and 18 will bind thereto. As illustrated, a sample containing all of IgG, IgA and IgM specific for HIV are captured by HIV immobilized at second immobilized assay reagent area 16. IgG of all specificities has been captured at first immobilized assay reagent area 12 by immobilized Protein A. (This serves as a control, as IgG is present in large amounts in all serum samples.) If no infection is present, that is, if no antibodies to HIV are present in the sample, species in the sample will not bind to the immobilized HIV at area 16. Inevitably, some sample components will remain at test assay surface 10, unbound to any immobilized assay reagents, and this is indicated at 34.

Subsequently, delivering member 20 is removed and an excess of a detection reagent is deposited upon test assay surface 10. According to the assay illustrated, the detection reagent includes Protein A 36 coupled to a hydrophobic label, specifically indigo, which binds to IgG bound to Protein A at area 12 of surface 10, and to IgG bound to HIV at area 16 of surface 10. The reagent also includes anti-IgA-IgG 38 which binds to IgA bound to HIV at area 16 of surface 10, and anti-IgM-IgG 40, which binds to IgM bound to HIV at area 16 of surface 100 Indigo is hydrophobically coupled to each of anti-IgA-IgG 38 and anti-IgM-IgG 40, serving both as a label and a blocking agent blocking the binding site on each from interaction with Protein A 36.

The pore dimension of test assay solid phase 11 is most preferably from about 10 to about 20 microns. The relatively large pore size of test assay solid phase 11 and the resultant rapid rate of flow of the excess detection reagent through the solid phase 11 results in a reduction in non-specific binding. In addition, extraneous species 34 is swept through solid phase 11 from test assay surface 10, which eliminates the need for a wash step between the step of applying sample and the step of applying detection reagent. Additionally, the rapidity of application of sample to assay surface 10, followed by rapid introduction of detection reagent, allows insufficient time for significant non-specific binding to be established.

After the addition of the detection reagent, the presence of label at both first immobilized assay reagent area 12 and second immobilized assay reagent area 16 is indicative of a sample containing antibodies to HIV. The presence of label at first immobilized assay reagent area 12 only (i.e. no label at area 16) indicates the absence of antibodies to HIV.

Figure 2A:
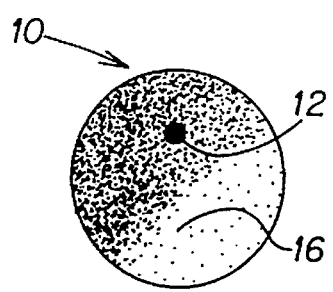
Figure 2B:
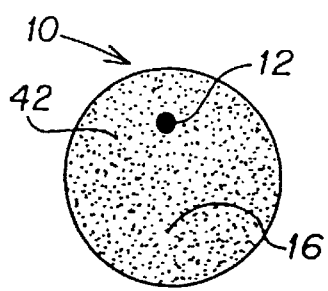
Figure 2C:
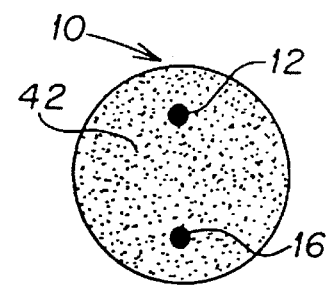

Referring now to FIGS. 2a–c, the appearance of test assay surface 10 after the assay illustrated in FIG. 1 has been performed. An error (a), a negative test (b), and a positive test (c), are illustrated. FIG. 2a indicates error as dye has been unevenly immobilized at surface 10, which indicates that serum has been unevenly applied to test assay surface 10. This indication is described more fully in the above-referenced, co-pending application entitled "Radial Flow Assay", by Dorval et al. Referring now to FIG. 2b, the presence of dye at area 12 and the presence of lightly shaded dye background across surface 10, and the absence of dye at area 16 signifies absence of infection. IgG has bound to Protein A immobilized at area 12 which has in turn been coupled to dye-coupled Protein A in the detection reagent. However, no antibody to HIV has been immobilized at area 16, indicated by the lack of labeled detection reagent immobilized at area 16. Referring to FIG. 2c, infection is indicated as labeled components in the detection reagent are bound at both areas 12 and 16, signifying the presence of antibodies to HIV in the serum sample bound to immobilized HIV at area 16. In all cases label bound at area 12 serves as a control according to the assay illustrated. That is, another indication of error (not shown) is an absence of any label at area 12.

The following examples are intended to illustrate the benefits of the present invention, but do not exemplify the full scope of the invention. For example, although dyes and pigments are exclusively exemplified as labels, as described above a variety of labels may be employed. While immobilization of antigen to detect antibodies specific for the immobilized antigen in a serum sample, with immobilization of protein to capture IgG as a control is exclusively exemplified, any of a variety of test assays may be carried out. The above-described and other modifications and their equivalents are understood to be within the scope of the present invention.

EXAMPLE 1

PROCEDURE FOR PRODUCING FROZEN STOCKS OF HIV1

In this and the following examples, all chemicals were obtained from Sigma Chemical Corporation (St. Louis, Mo.) unless otherwise noted.

Preparation of required solutions:

An LB solution was prepared by dissolving 5 grams of yeast extract (DIFCO/VWR), 10 grams of tryprone (DIFCO/VWR), and 10 grams of NaCl in 1 liter of MilliQ water, adjusting the pH to 7.2, and sterilizing by autoclaving. MilliQ water was obtained by filtration of water through a MilliQ water system (Millipore Corp., Bedford, Mass.). The solution was allowed to cool and Ampicillin was added to bring the final concentration to 0.1 mg/ml.

SOB Broth was prepared by dissolving 5 grams of yeast extract and 20 grams of tryprone in 1 liter of MilliQ Water containing 10 ml of a 1M NaCl stock, and the pH was adjusted to 7.5. The solution was autoclaved and allowed to cool. The final solution was adjusted to 20 mM $MgCl_2$/$MgSO_4$, by the addition of 10 ml of a 1M $MgCl_2$ stock and 10 ml of a 1M $MgSO_4$ stock.

FSB solution was prepared as described in Maniatis (Molecular Cloning), §1.78. The following components were added to MilliQ water: 10 ml of 1M potassium acetate (pH 7.5), 8.91 g of $MnCl_2·4H_2O$, 1.47 g of $CaCl_2·2H_2O$, 7.46 g of KCl, 0.80 g of hexaminecobalt chloride, and 100 ml of glycerol (Amresco). The solution was adjusted to 1 liter with MilliQ water and the pH adjusted to 6.4 with 0.1N HCl (J. T. Baker, Phillipsburg, N.J.).

Preparation of E. Coli HIV1 stocks:

LB Broth (10 ml) was innoculated with 0.2 ml of a glycerol (Amresco) stock and then grown overnight in an incubator shaker at 28° C. and 300 RPM. The overnight culture was added to 200 ml SOB containing 20 mM $MgCl_2$/$MgSO_4$ in a 1 Liter Pyrex Fernbach Flask and the mixture was grown until the optical density was 0.6 to 0.7. The cells were then transferred to sterile, disposable, ice-cold 50 ml polypropylene tubes (Falcon) and the cultures cooled to 0° C. by storing the tubes on ice for 10 minutes. The remaining steps were carried out aseptically.

The cells were recovered by centrifugation at 4000 rpm for 10 minutes at 4° C., using a TZ-28 rotor (Sorvall) in a RC-5B centrifuge (Sorvall). After the supernatant was completely removed and discarded, the pellet was resuspended by gentle vortexing, in approximately 80 ml (20 ml per 50 ml tube) of ice-cold FSB. The cells were allowed to stand on ice for 10 minutes and were recovered by centrifugation at 4000 rpm for 10 minutes at 4° C. After the supernatant was completely removed and discarded, the pellet was resuspended by gentle vortexing in approximately 20 ml (5 ml per 50 ml tube) of ice-cold FSB. 0.7 ml (175 ul per 50 ml tube) of DMSO was gently mixed into the solution and the suspension was returned to an ice bath. An additional 175 ul (per 50 ml tube) of DMSO was added to the suspensions, mixed gently and then returned to an ice bath. The suspensions were aliquoted (0.2 mls) into chilled, sterile microfuge tubes and then frozen by immersion of the tightly closed tubes in a methanol dry ice bath. The tubes were stored at −80° C. until needed.

Production of HIV1 from a frozen DMSO stock:

At least two days after freezing the cells, the high yield induction of HIV1 from a starter culture, which was grown from a frozen DMSO stock, may be determined. In order to perform this analysis the stock was removed from an −80° C. freezer and thawed on ice. 0.2 ml of cells were added to 1 ml of SOB medium, and then incubated for 1 hour at 28° C. The starter culture was prepared by adding this 1.2 ml culture to 200 ml LB medium (0.1 mg/ml Ampicillin (Amresco)) and incubating at 28° C. overnight. The HIV1 was then purified as described in Example 2.

EXAMPLE 2

PROCEDURE FOR PRODUCING AND PURIFYING HIV 1

Preparation of required solutions:

LB Broth was prepared by dissolving 17 grams of yeast extract (DIFCO/VWR), 34 grams of tryprone (DIFCO/VWR), and 34 grams of NaCl in 3.4 liters of MilliQ water (Millipore Corp.), adjusting the pH to 7.2, and sterilizing by autoclaving. The solution was allowed to cool and Ampicillin (Amresco) was added to a final concentration of 0.1 mg/ml.

One Liter of 50 mM Tris-HCl, 2 mM EDTA, pH 8.0 was prepared as follows: 6 grams of TRIZMA BASE and 744 milligrams of EDTA were dissolved in MilliQ water (Millipore Corp.), the pH was adjusted to 8.0 with HCl (J. T. Baker), and the final volume of the solution was adjusted to 1 liter with MilliQ water.

In order to prepare one liter of Extract Buffer 480.5 grams of UREA (8M) (Amresco), 4.08 grams of BICINE (25 mM), 1.54 grams of DTT (10 mM), and 1.86 grams of EDTA (5 mM) were dissolved in MilliQ water containing 1 ml of TWEEN 20 (0.1%, polyoxyethylene sorbitan monolaurate, Calbiochem, La Jolla, Calif.). The pH of the solution was brought to 8.5, and the volume was adjusted to one liter with MilliQ Water.

One liter of 25% Ammonium Sulfate was prepared by dissolving 250 grams of ammonium sulfate in one liter of MilliQ water.

Growth of and induction of 3 liters of *E. coli* containing HIV1:

The culture from Example 1 was innoculated into a 1 Liter Pyrex Fernbach Flask containing 200 ml LB Broth, and grown overnight in an incubator shaker at 25° C. and 300 RPM. 10 ml of this culture was saved and stored at 4° C. for an experimental control (UNINDUCED CONTROL). The next day 50 ml of the culture was used to innolculate 3×2.8 Liter Pyrex Fernbach Flasks each containing 1 liter LB Broth. The cultures were grown in the incubator shaker at 30° C. and 300 RPM until the OD was 0.6–1.0 at 600 nm (2 to 3 hours).

The cultures were removed from the 30° C. incubator shaker and a 160–170 ml aliquot was transferred into a sterile 0.5 Liter Pyrex Fernbach Flask. The temperature of the culture aliquot was quickly raised by transferring the 0.5 liter flask into a 60°–70° C. water bath. While it was immersed in the water bath the flask was shaken and the temperature of the culture inside was monitored. As soon as the culture reached 42° C. (after 2 to 3 minutes), the contents of the flask was transferred into a preheated 2.8 Liter Pyrex Fernbach Flask (6 empty, sterile 2.8 Liter Pyrex Fernbach Flasks were preheated in a shaker at 42° C. and 200 RPM). This procedure was repeated until each of the 6 flasks contained 0.5 liters of induced culture. The flasks were covered and the shaker speed was raised to 400 RPM. A 1 ml aliquot was removed from each of the 6 flasks and saved as an experimental control for induction (INDUCED CONTROL). The cultures were incubated at 42° C. and 400 RPM overnight. The next day the cells were harvested by centrifugation in a rotor (Sorvall) in a Sorvall RC-5B centrifuge at 8000 RPM for 20 minutes. If the cells were not required for immediate purification, they were stored at −80° C.

Extraction and purification of inclusion bodies:

The cell pellet was thawed and resuspended in a total of 300 ml of 50 mM Tris-HCl pH 8.0, 2 mM EDTA (100 ml/1 L culture ratio). In order to enable efficient resuspension, the solution was sonicated (Branson sonifier Model 450) and lysozyme was added to a final concentration of 100 mg/ml (3 ml of a 10 mg/ml stock freshly prepared in 50 mM Tris-HCl pH 8.0, 2 mM EDTA was used). 1/100 of a volume of 10% Triton X-100 (3 ml) was added, and the solution was incubated at 30° C. for 15 minutes. The solution was then cenrifuged in a Sorvall RC-5B at 8000 RPM in a GS-3 rotor for 1 hour. If the supernatant was not clear the centrifugation was continued for another hour or the solution was spun at 15000 RPM in a TZ-28 rotor. The supernatant was collected and stored at 4° C. until an aliquot (100 uls) had been analyzed by Polyacrylimide Gel Electrophoresis (PAGE) (LYSOZYME SUP). The pellet was resuspended with sonication in a total of 300 ml of 50 mM Tris-HCl pH 8.0, 2 mM EDTA (100 ml/1 L culture ratio) and 100 ul was removed (LYSOZYME PREC) for PAGE analysis. Centrifugation was performed as described above (in a Sorvall RC-5B at 8000 RPM in a GS-3 rotor (Sorvall) for 1 hour) and 100 ul of the supernatant was removed for PAGE analysis (WASH SUP). The pellet was resuspended with sonication in a total of 60 ml of Extract Buffer (20 ml/1 L culture ratio). A 20 ul aliquot was saved for an experimental control (EXTRACT 1). The cell suspension was then centrifuged in a Sorvall RC-5B at 15000 RPM in a TZ-28 rotor for 30 minutes. The supernatant was transferred to a fresh tube for further purification (SOLUTION 1). The pellet was resuspended in 30 ml of Extract Buffer and centrifuged as described in the previous step (15000 RPM in a TZ-28 rotor for 30 minutes). Before centrifugation a 20 ml aliquot was removed for an experimental control (EXTRACT 2). The supernatant was transferred to a fresh tube for further purification (SOLUTION 2). 20 ml aliquots of SOLUTION 1 and SOLUTION 2 were removed for an experimental control.

SOLUTION 1 and 2 were combined and the inclusion bodies were precipitated by adding 5 volumes of 25% Ammonium Sulfate (450 ml). The solution was centrifuged in a Sorvall RC-5B at 8000 RPM using a GS-3 rotor (Sorvall) for 1 hour. If the supernatant was not clear the centrifugation was continued for another hour or the solution was centrifuged at 15000 RPM in a TZ-28 rotor. A 20 ul aliquot of the supernatant was removed for use as an experimental control (SOLUTION 3). The pellet was resolubilized by the addition of 60 ml of Extract Buffer with sonication. A 20 ul aliquot of the resuspended pellet was removed for an experimental control (EXTRACT 3). The solution was precipitated with 300 ml (5 volumes) of 25% Ammonium Sulfate and centrifuged as described above (at 8000 RPM in a GS-3 rotor (Sorvall) for 1 hour). A 20 ul aliquot of the supernatant was removed for use as an experimental control (SOLUTION 4). The pellet was resuspended with sonication in 100 ml (1/30 of the original culture volume) of Extract Buffer (INCLUSION BODIES).

Purification of HIV1 by electroelution:

13 ml Glycerol (Amresco) and 13 ml of 10% SDS (GIBCO BRL, Helgerman, Conn.) were added to the suspension of inclusion bodies (100 ml) obtained in the previous step and aliquots of 16–17 ml were removed for electrophoresis. The remainder of the samples were stored at 4° C. (or at −80° C. for long-term storage).

Preparative SDS Polyacrylamide Gels (37 mm ID) were prepared as described in the BIO-RAD Model 491 Prep Cell Instruction Manual (pages 13–15). 80 ml (10 cm) of a 12% Separating Gel solution and 28 ml (3.5 cm) of Stacking Gel solution were used to pour the gels. The Model 491 Prep Cell (BIO_RAD) was assembled and operated according to the Instruction Manual (pages 15–20). Prior to loading, 50 ul of sample buffer containing Bromophenol Blue and 160 ul of b-Mercaptoethanol were added to each 16–17 ml aliquot of sample. The sample was heated to 90° C. for 10 minutes (this was done by transferring small aliquots of the sample into eppendorf tubes and placing them into a heat block). A total of 16–17 ml of sample was loaded onto each preparative gel. After loading, the Model 491 Prep Cells was operated under a constant current of 40 mA, for 22 h, with an elution buffer flow rate of 30 ml/h (0.5 ml/min), and fractions were collected for 20 min.

10 ul aliquots of sample were collected after the elution of the Bromophenol Blue. These aliquots were run on a 12% SDS (GIBCO/BRL) polyacrylamide gel in order to determine which of them contained the 27.3 kd HIV1 protein. The fractions containing HIV1 were then pooled and further purified by precipitation and resuspension as described below.

The experimental controls were processed as described for each control and 10 ul aliquots of each sample were run on 12% SDS (GIBCO/BRL) polyacrylimide gels under reducing conditions.

INDUCED AND UNINDUCED CONTROLS: Each sample was transferred to an eppendorf tube and spun to separate out insoluble material. The supernatant was discarded and the pellet was resuspended in 0.1 ml MilliQ water.

LYSOZYME SUP, LYSOZYME PREC, SOLUTION 1,2,3 & 4 and EXTRACTS 1, 2 & 3: These controls were diluted with 80 ul of water and run in 10 ul aliquots on PAGE gels.

Precipitation and resuspension of HIV1 for test assay surface blotting:

The pooled HIV1 fractions from electroelution were added to a new centrifuge tube (50 ml, Sarstedt, Newton, N.C.; 250 ml, Corning, Corning, N.Y., or equivalent) which is capable of holding three times the starting volume. Two volumes of 100% ethanol were added to the fraction and mixed well. After incubation for at least 30 minutes at room temperature, the suspension was centrifuged in a Sorvall RC-5, SS34 rotor (Sorvall) at 4000 rpm for 30 minutes, with no brake. The supernatant was decanted and saved, and the tube was inverted to blot off all fluid. The pellet was white, waxy and shiny with a very smooth texture (i.e. not granular). The pellet was resuspended in the smallest amount of 0.1N NaOH possible. To do this, the NaOH must be added in 200 ul increments until there are no visible solids remaining. The solution was then centrifuged in a microfuge for 5 minutes to remove any remaining solids. The protein concentration of this solution was determined and then 5 ug/lane of sample were run on a 15% SDS-PAGE reduced and non-reduced. 0.5 ul containing 2 ug of HIV1 was then be blotted as described in Example 4.

EXAMPLE 3

PREPARATION OF AMYLOSE COLUMN AND ELUTE BUFFER AND PROCEDURE FOR PRODUCING AND PURIFYING HIV 2

Preparation of required solutions:

Amylose column buffer was prepared by dissolving 1.2 grams of trizma base, 11.7 grams of NaCl, and 372 milligrams of EDTA in 900 ml of MilliQ water. Once the chemicals were completely dissolved 700 ul of b-mercapatoethanol was added and pH was adjusted to 7.4 (within 0.1) with 10N HCl. Sterilization was accomplished by filtration of the solution through a 0.45 mm filter unit (Costar, Cambridge, Mass.). The sterile solution was stored at 4° C. This solution should not be used if stored for longer than 30 days.

Amylose elute buffer was prepared by dissolving 1.2 g of Trizma base, 11.7 g of NaCl, 372 mg of EDTA, and 3.42 g of Maltose in 900 ml of MilliQ water. Once the chemicals were completely dissolved 700 ul of b-mercapatoethanol was added and the pH of the solution was adjusted to 7.4 (within 0.1) with 10N HCl (J. T. Baker). The solution was sterile filtered through a 0.45 mm filter unit and stored at 4° C. This solution should not be used if stored for longer than 30 days.

LB Broth was prepared by dissolving 5 grams of yeast extract (DIFCO/VWR), 10 grams of tryptone (DIFCO/VWR), and 10 grams of NaCl in 1 liter of MilliQ water, adjusting the pH to 7.2, and sterilizing by autoclaving. The solution was allowed to cool and Ampicillin (Amresco) was added to a final concentration of 0.1 mg/ml. One liter of LB broth was aliquoted into each of 6, 2.8 Liter Pyrex Fernbach Flasks and 400 ml of LB Broth was aliquoted into a 1 Liter Pyrex Fernbach Flask.

100 ml of 100 mM isopropylthio-b-D-galactoside (IPTG)

500 ml of 20% Ethanol (V/V)

8 Liters of 1X Phosphate Buffered Saline (PBS) pH 7.2

Growth of 6 liters of *E. coli*/MBP construct:

A 1 Liter Pyrex Fernbach Flask containing 400 ml LB Broth (100 mg/ml Ampicillin, Amresco) was innoculated with the transfected culture and grown overnight in the incubator shaker at 37° C. and 250 RPM. 10 ml of this culture was saved at 4° C. for an experimental control (UNINDUCED) Each of 6, 2.8 Liter Pyrex Fernbach Flasks containing 1 liter of LB Broth were innoculated with 50 ml of culture grown in the previous step. Cultures were grown in the incubator shaker at 37° C. and 250 RPM until the O.D. at 600 nm was between 0.6 and 1.0 (2 to 2.5 hours). 3 ml of culture were removed for SDS-PAGE analysis of induction (UNINDUCED 2).

The cultures were induced by adding 10 ml of 100 mM IPTG to each flask. The flasks were covered and incubated for 3 hours at 37° C. and 250 RPM. The final O.D. was measured and an aliquot of 3 ml of culture was removed for SDS-PAGE analysis of induction (INDUCED). The cells were harvested by centrifugation in the Sorvall RC-5B at 8000 RPM for 20 minutes. If cells were not required for immediate purification, they were stored at −80° C.

Induction was analyzed by electrophoresis of the control samples isolated in the above steps. 1 ml of the UNINDUCED, UNINDUCED 2, and INDUCED samples were spun in a microcentrifuge and the pellets were resuspended in 100 ul of MilliQ water. 10 ul aliquots of these cell suspensions are run on a 15% SDS-PAGE gel under reducing conditions.

Extraction of inclusion bodies:

The cell pellet was thawed and resuspend in Amylose Column Buffer at a ratio of 10 ml per every gram of pellet. The samples were sonicated until total suspension was achieved. The suspension was kept chilled by storage in an ice bath during sonication. Once totally suspended, the samples were incubated at room temperature on a tumbler or rocking platform for 4 hours (or overnight). However, one ml of the suspension was saved for SDS-PAGE analysis of the extraction (SOLUTION 1).

The samples were transferred to high speed centrifuge tubes and centrifuged in a Sorvall RC-5B (TZ-28 rotor) at 18000 RPM for 20 minutes. The supernatant was decanted into a 250 ml conical tube and diluted with an equal volume of Amylose Column Buffer. The mixture was then sterile filtered using a 500 ml 0.45 mm filter unit. The filtered solution contains the cell-free extract (CFE).

Aliquots of SOLUTION 1 and CFE were run on a gel to determine the efficiency of the above procedures. 0.5 ml of SOLUTION 1 was aliquoted into a new eppendorf tube and spun to pellet in the microcentrifuge. The supernatant was discarded and the pellet was resuspended in 0.5 ml of MilliQ water. A 5 ul aliquot of the pellet suspension of SOLUTION 1 along with 5 ul of CFE was run on a 15% SDS-PAGE gel under reducing conditions.

Purification of MBP construct on amylose column:

A 2.5 cm×30 cm HPLC column (Amicon, Beverly, Mass.) was assembled with a Peristaltic Pump (Pharmacia LKB Pump P-1, Piscataway, N.J.), UV Detector (Pharmacia LKB Uvicord SII), and Chart Recorder (Pharmacia LKB Recl). Once the equipment was warmed up (30–60 minutes before use), 60–80 ml of Amylose resin was poured over the column and the column was packed by passing through 4–5 column volumes of MilliQ water. The resin was equilibrated with 2 column volumes of Amylose Column Buffer.

The chart recorder was started and once a stable baseline was achieved, the CFE was loaded using Pump Setting 4 (×10). 100 ml aliquots of the flow through (FT) was collected in 250 ml conical tubes (Corning/VWR, Corning, N.Y.) (Fractions which are collected after the saturation of the column was reached were run over another column) Once the whole CFE had passed the resin, the column was washed with Amylose Column Buffer until the baseline was reached.

Once baseline was achieved, the Amylose Elute Buffer was run through the column. The construct began to elute in the first 3–5 fractions causing a sharp peak to appear on the chromatogram. The fractions were collected until baseline was reattained.

The purity of the peak fractions was determined by running 2–5 ul aliquots of each fraction, varying the amount depending on the strength of the peak (very weak peak requiring more sample), on a 15% SDS-PAGE gel under reducing conditions. The 2 fractions flanking each peak as well as the FT fractions were also run. The FT fractions was run in order to determine if the saturation of the resin was reached. If saturation was reached, the whole flow through or part of it was run over a second column. If the protein was >90% pure as estimated by SDS-PAGE, the peak fractions were pooled and dialyzed in dialysis membrane of MWCO 25,000 (Spectrum, Los Angeles, Calif.), against four liter volumes of 1X PBS pH 7.2 at 4° C. At least four hours was allowed for each cycle. If significant impurities were present, SDS-PAGE and Western Blot Analysis were performed on the dialyzed protein.

The Amylose Resin was reused up to five times before losing its binding capacity. Storage of the column was done in 20% Ethanol (Aaper Alcohol, Shelbyville, Ky.) by running 2–3 column volumes through the resin and storing at room temperature.

EXAMPLE 4

PREPARING HIV 1 AND HIV2 IMMOBILIZED ON A TEST ASSAY SURFACE

A porous, nitrocellulose membrane (Millipore 704, 10–20 um, SA3M214H2, nitrocellulose), to which HIV1 and HIV2 antigens were to be attached, was cut into 20 mm squares and placed on a piece of blue interleaf on a benchtop. The front of each square at the bottom center was marked to insure that the blotted side was up and the orientation was clear. The HIV1 antigen was diluted to 8 mg/ml with 0.1N NaOH and the HIV2 antigen was diluted with 0.2 um filtered distilled water (FDW) to 4 mg/ml. An equal volume of HIV2 solution was added to the HIV1 solution and mixed well without foaming (HIV ½ combo-antigen). Protein A (Repligen, RPA-100) was dissolved at 1 mg/ml in FDW for a control. These solutions were prepared fresh and used the same day.

0.5 ul of the HIV ½ protein solution was blotted onto the test assay surface at the bottom center (near the identification mark) and 0.5 ul of the Protein A was blotted at the top center. The blots were spaced in the center of the test assay surface, without any overlap, and allowed to dry for at least 30 minutes at room temperature. The blotted membranes were stored at 4° C. in a zip-lock bag.

EXAMPLE 5

PROCEDURE FOR BLOCKING PREFILTER

A porous, nitrocellulose prefilter membrane (Millipore, HATF 08250, 0.45 um, nitrocellulose) was cut into 20 mm squares, and submerged in PBS containing 5% fetal bovine serum (FBS, JRH# 12-10378P) for 20 minutes. The resultant individual filters were then removed from blocking buffer, dipped in PBS to wash off the excess FBS, and transferred to PBS-2% polyethylene glycol (PEG; 3000–3700 MW). Once the filters were removed from the PBS-PEG they were placed on dry filter paper and allowed to dry at least 30 minutes at room temperature. The membranes were stored at 4° C. in a zip-lock bag.

EXAMPLE 6

PROCEDURE FOR ASSEMBLING DELIVERING MEMBER

A porous diffusing material was formed of a membrane (Millipore 704, 10–20 um, SA3M214H2, nitrocellulose) which was cut into 20 mm squares. Each square was placed on the sticky side of the top half of a two-piece adhesive label, or tab, so as to completely cover a 1.5 cm hole in the label. The top half was marked with typing to distinguish it from the bottom half of the label. The blocked test assay surface membranes from Example 5 were removed from the plastic bag (Millipore, HATF 08250, 0.45 um, nitrocellulose; in some cases Millipore HAHY0000 was used). Each was tamped onto a 1.5 cm hole on the sticky side of the bottom half of the label, which was not marked with any typing. Both membranes were carefully tamped onto the sticky sides of the labels to insure even contact. The labels were carefully stuck together (adhesive sides facing each other) so that the label holes were aligned and then any excess membrane was trimmed off. The label halves thus define a connector, holding the diffusing membrane and prefilter membrane in face to face relation. This assembled delivering member was stored at 4° C. in a zip-lock bag.

EXAMPLE 7

PROCEDURE FOR ASSEMBLING TEST ASSAY KIT

A plastic base having a cavity approximately 0.7 cm deep, 2.1 cm wide and 3.5 cm long was obtained from Porex Technologies. At the bottom of the cavity, a dome approximately 0.3 cm high, with a diameter of approximately 1.5 cm was formed in an upward direction. An urging member in the form of an absorbent material, specifically a cotton ball, was pressed into the cavity of the base so that the cotton was about half an inch above the top of the base. On top of the cotton, was placed one blotted-membrane from Example 4 and on top of that was placed one prefilter (prefilter from Example 6). A plastic cover, also from Porex Technologies, including an opening approximately 1.0 cm in diameter, and forming a well immediately about the opening, was then placed over the membranes so that they were centered within the opening. The top was pressed down and riveted into place. The membrane appeared with a slight "dome" which, when pressed, was very firm, indicating that the device was packed correctly. That is, the test assay surface of the test assay solid phase (blotted membrane of Example 4) was held in even contact with the delivering surface of the delivering member. Similarly, the diffusing membrane and prefilter membrane of the delivering member, held in face to face relation with the label connector of Example 6, were held in even contact according to this arrangement.

EXAMPLE 8

PROCEDURE FOR PRODUCING PROTEIN A LABELED WITH INDIGO

Indigo (Aldrich, 22,929-6) was placed into a mortar and ground with a pestle until the powder was very fine and uniform (about 15 minutes). 1.5 gm of ground Indigo was suspended in 300 ml of milliQ water in a 500 ml Erlenmeyer flask and the solution was heated at 65° C. for 10 minutes. The solution was sonicated for 90 minutes (Branson 450, duty cycle 70, output 4) and then allowed to come to room temperature (about 90 minutes). The pH of the solution was adjusted to pH 5.5 using 0.1N HCL. 1 mg/ml solution of Protein A (Repligen, RPA-100) was prepared in D-H$_2$O and 1.75 ml was added to 35 ml of the Indigo suspension in a 50 ml tube (Nalgene polypropylene-capped, 8 tubes required). This gave a 50 ug/ml solution. After incubating for 10 minutes at room temperature the solution was centrifuged at 18000 rpm for 50 minutes in an SS34 rotor (Sorvall, RC-5).

The supernatant was removed and the pellet was resuspended in 30 ml of 10 mM Na$_2$HPO$_4$, pH 7.4 containing 0.5M NaCl and 1% BSA (PBSBSA). This solution was centrifuged at 18000 rpm for 25 minutes in an SS34 rotor (Sorvall, RC-5) and the pellet was resuspended in 30 ml of PBSBSA containing 10% glycerol (PBSBSAG). The solution was again centrifuged at 18000 rpm for 25 minutes in an SS34 rotor (Sorvall, RC-5) and the pellet was resuspended in 30 ml of PBSBSAG. The solution was filtered through an 8 um filter (Whatman). This took about 20 minutes and resulted in very little loss of material. Then the solution was filtered through a 2 um filter (Whatman). This took about 1 hour and resulted in approximately 30% loss of material. 4 ul of PAI was added to 750 ul of D-H$_2$O and the OD$_{610}$ was adjusted to 0.0075 with PBSBSAG. 1.5 ml of the diluted PAI was aliquoted into vials (Sarstedt, 72730-005) and stored at 4° C.

EXAMPLE 9

PROCEDURE FOR PRODUCING ANTI-IgM-IgG AND ANTI-IgA-IgG LABELED WITH INDIGO 2 g of Indigo (Aldrich, 22,929-6) was placed into a mortar and ground with a pestle until the powder was very fine and uniform (about 15 minutes). 1.5 g of the ground Indigo was suspended in 300 ml of MilliQ water in a 500 ml Erlenmeyer flask, covered with tin foil. The solution was heated at 65° C. for 10 minutes and then allowed to come to room temperature (about 90 minutes). The pH of the solution was adjusted to pH 5.5 using 0.1N HCL. A 450 ug/ml solution of Antibody was prepared as follows: 12 ml Bethyl Goat anti-Human IgA #A920-6 (Affinity Purified) @ 3.4 mg/ml was added to 16 ml Bethyl Goat anti-Human IgM # M21-6 (Affinity Purified) @ 2 mg/ml with a total volume of 28 ml and a total of 78 mg. 18 ml of the Indigo suspension was placed into eight 40 ml tubes (Sorvall, 03530) and 3.5 ml of Ab combo was added to each tube, resulting in a 500 ug/ml solution. The solution was then incubated for 30 minutes at room temperature before centrifugation (Sorvall, RC-5 with SS34 rotor) at 18000 rpm for 50 minutes. The supernatant was removed and the pellet was resuspended in 18 ml of 10 mM Na$_2$HPO$_4$ (Sigma), pH 7.4 containing 0.5M NaCl (Sigma) and 1% BSA (Miles, Pentax, Fract V, 81003-40 [PBSBSA]). This solution was centrifuged at 18000 rpm for 25 minutes in an SS34 rotor (Sorvall, RC-5) with the brake off. The pellet was resuspended in 18 ml of PBSBSA containing 10% glycerol (Amresco, 0854) (PBSBSAG). This solution was again centrifuged at 18000 rpm for 25 minutes in an SS34 rotor (Sorvall, RC-5) with the brake off, and the pellet was resuspended in 18 ml of PBSBSAG. The solution was filtered through an 8 um filter (S&S Immobilization membrane, #AE99), followed by a 5 um filter (MSI, magna nylon transfer membrane), then a 2 um filter (Millipore, Immobilion AV-2, SA3J898E8). The OD of the solution was checked by measuring at 610 nm. 8 ul of Ab-I was added to 1.5 ml PBSBSAG and the OD was adjusted to 0.03 with PBSBSAG. For example, if the 8 ul gave an OD of 0.12 the PAI was diluted 1:4 with PBSBSAG. NaN$_3$ was added to a final concentration of ug/ml and the solution was stored at 4° C.

EXAMPLE 10

PROCEDURE FOR PRODUCING DETECTION REAGENT 15.6 mls of IMA (Solution obtained in Example 9) was mixed with 109.4 mls of IPA (Solution obtained in Example 8). 375 mls of PBSBSAG containing 40 ug/ml of NaN$_3$ was added to this solution. The total volume was 500 mls and the solution had an $OD_{610}$=0.015. 500 mls of PBSBSAG containing 40 ug/ml of $NaN_3$ was added and the final solution had an $OD_{610}$=0.0075.

EXAMPLE 11

PROCEDURE FOR PRODUCING PROTEIN A, ANTI-IgA, ANTI-IgM-PIGMENT DETECTOR 100 mg of pigment, either Red 17=part #235-7515; Violet 23=part #246-1670 or Green 7=part #264-3120; from Sun Chemical, 4526 Chickering Avenue, Cincinnati, Ohio 45232, was measured out and placed into a 50 ml conical tube (Sarstedt). One of the following was added to the tube containing the pigment: 1) 20 ml of a 1 mg/ml-distilled water solution of Protein A (RPA-100, Repligen), 2) 6 ml of Goat anti-Human IgA (A80-102A, Lot A92G, 3.4 mg/ml, Bethyl Labs, Montgomery, Tex.), or 3) 8 ml of Goat anti-Human IgM (A80-100A, Lot M121G, 2.0 mg/ml, Bethyl Labs). The material in each vial was suspended by inversion but it was done with care so as not to create too much foam (about 30 minutes). The suspension which was clumpy and not well suspended contained fluid which was clear and did not take on the color of the pigment. Each tube was brought to a final volume of 45 ml by adding PBSBSAG (10 mM $Na_2HPO_4$, 0.5M NaC), 1% BSA:#81003-40, Miles, Pentax, 10% Glycerol:#0854-1, Amresco). The material in each vial was suspended by inversion and by crushing the clumps with a stainless-steel spatula, while taking care not to create too much foam (approx 15 minutes). The suspension which started to take on the color of the pigment but which was still clumpy and not well suspended, was incubated at room temperature for 45 minutes, and then centrifuged at 18000 rpm for 25 minutes, with the brake off (Sorvall, RC-5 centrifuge, SS34 rotor using 50 ml tubes, Sorvall, #03530). The supernatant was removed and the was pellet resuspend in 100 ml PBSBSAG. The suspension was first filtered through an 8 um filter (S&S, AE99) and then through a 2 um filter (Milliport. Immobilion AV-2, SA31898E8). $NaN_3$ was then added to the solution to a final concentration of 20 ug/ml.

EXAMPLE 12

TEST ASSAY 120 ul of a serum sample was added directly onto the center of the delivering member of the test assay kit of the present invention. After from 10 to 15 seconds, the delivering member was removed and discarded. 1.5 ml (0.015 OD units) of the detection reagent of Example 10 was added into the well and allowed to flow through the membrane (about 10 seconds). The results were recorded.

EXAMPLE 13

COMPARATIVE POSITIVE, NEGATIVE, AND ERROR RESULTS USING AN ASSAY KIT 120 ul of each of a positive and negative HIV serum sample was added to the center of a delivering member of a test assay kit prepared in accordance with the present invention. After from 10 to 15 seconds, in each case, the prefilter was removed and discarded. In each case, 1.5 ml of the detection reagent prepared in accordance with Example 10 was added into the assay kit well and allowed to flow through the test assay membrane, which was completed in about 10 seconds. FIG. 2c illustrates the appearance of the test assay surface to which a positive serum sample had been applied, following the application of the detection reagent. FIG. 2b illustrates the appearance of the test assay surface to which a negative serum sample had been applied, after application of the detection reagent. As a comparative (error) example, the prefilter was removed from a test assay kit prepared in accordance with Example 10 and the test assay surface was wetted unevenly with a negative serum sample. That is, a portion of the test assay surface was contacted with serum to a greater extent than another portion. Subsequently, 1.5 ml of the detection reagent prepared in accordance with Example 10 was added allowed to flow through the test assay membrane. The results are illustrated in FIG. 2a. The unevenness of the distribution of the label on the test assay surface can be measured with the naked eye, indicating the unevenness of the serum application to the test assay surface.

The preceding examples are set forth to illustrate the specific embodiments of the invention and are not intended to limit the scope of the invention. Additional embodiments and advantages within the scope of the claimed invention will be apparent to those of ordinary skill in the art.

What is claimed is:

1. A detection reagent for use in a test assay, comprising:
   an immunoglobulin, belonging to a class, that specifically binds to a predetermined analyte;
   a labeled protein that specifically binds to a binding site on an Fc region of immunoglobulins of the class, which protein is not bound to the analyte to which the immunoglobulin specifically binds; and
   a blocking agent that is hydrophobically coupled to the immunoglobulin and that blocks the binding site from interaction with the protein,
   wherein the immunoglobulin is labeled and the immunoglobulin, the labeled protein, and the blocking agent are together contained in the detection reagent formulated to detect at least the predetermined analyte.

2. The detection reagent as recited in claim 1, wherein the protein is selected from the group consisting of Protein G and Protein A, and the immunoglobulin comprises IgG.

3. The detection reagent as recited in claim 1, wherein the blocking agent comprises the label on the immunoglobulin.

4. The detection reagent as recited in claim 3, wherein the label is selected from the group consisting of dyes and pigments.

5. The detection reagent as recited in claim 1, wherein the immunoglobulin is selected from the group consisting of anti-IgA of the IgG class and anti-IgM of the IgG class, and the protein comprises protein A.

6. The detection reagent as recited in claim 5, wherein the Protein A is labeled with one of a dye or pigment hydrophobically coupled to the Protein A.

7. The detection reagent as recited in claim 1, wherein the protein comprises a second immunoglobulin.

8. The detection reagent as recited in claim 7, wherein the immunoglobulin comprises IgG and a second immunoglobulin comprises anti-IgG of the IgG class.

9. An article of manufacture comprising:
   a support having hydrophobic regions;
   an immunoglobulin coupled to the support via hydrophobic coupling between an Fc binding site of the immunoglobulin and one of the hydrophobic regions, the immunoglobulin belonging to a class; and
   a protein that specifically binds to a binding site on an Fc region of immunoglobulins of the class and that is coupled to the support at essentially the same region of the support at which the immunoglobulin is coupled to the support, wherein the binding site for the protein on the Fc region of the immunoglobulin is blocked and the immunoglobulin and protein are free of hydrophobic coupling between them.

10. The article as recited in claim 9, wherein the support is selected from the group consisting of plates, water insoluble particulate species, gels, silica, alumina, porous membranes, and laboratory apparatus surfaces other than those recited above.

11. The article as recited in claim 10, wherein the support is selected from the group consisting of a dye particle and a pigment particle.

12. A method of capturing a specific binding partner of an immunoglobulin belonging to a class in the presence of a protein that specifically binds to a binding site on an Fc region of immunoglobulins of the class, comprising:

contacting a sample suspected of containing the specific binding partner with the immunoglobulin in the presence of the protein, the binding site on the Fc region of the immunoglobulin being blocked; and allowing the binding partner to specifically bind to the immunoglobulin, wherein the protein is not bound to the specific binding partner of the immunoglobulin.

13. The method as recited in claim 12, the contacting step comprising contacting the sample with the immunoglobulin hydrophobically coupled to a support to which the protein is also coupled.

14. The method as recited in claim 13, wherein the support is selected from the group consisting of dye particles and pigment particles.

15. The method as recited in claim 13, wherein the immunoglobulin is IgG, and the protein is Protein A.

16. The method as recited in claim 12, wherein the binding site is blocked with a blocking agent hydrophobically coupled to the immunoglobulin.

17. The method as recited in claim 16, wherein the blocking agent comprises a label.

18. The method as recited in claim 17, wherein the label is selected from the group consisting of dyes and pigments.

19. In an immunoassay method involving contacting a solution suspected of containing a plurality of analytes with a plurality of labeled binding partners for the analytes and determining the presence of one of the plurality of analytes, the improvement comprising:

contacting a solution suspected of containing a plurality of analytes with labeled Protein A and labeled IgG specific for the predetermined analyte.

20. A kit comprising:

a protein that specifically binds to a binding site on an Fc region of immunoglobulins of a class; and an immunoglobulin of the class, that specifically binds to a predetermined analyte, a binding site for the protein on the immunoglobulin being blocked with a blocking agent, wherein the protein and the immunoglobulin each are labeled and are both contained in a package and are not bound to each other.

21. The kit as recited in claim 20, wherein the binding site for the protein on the immunoglobulin is blocked with a blocking agent hydrophobically coupled to the immunoglobulin.

* * * * *